United States Patent [19]

Zupancic

[11] 4,246,482
[45] Jan. 20, 1981

[54] COMPUTED TOMOGRAPHY METHOD AND APPARATUS

[75] Inventor: Anton Z. Zupancic, Kirtland, Ohio
[73] Assignee: Picker Corporation, Cleveland, Ohio
[21] Appl. No.: 917,068
[22] Filed: Jun. 19, 1978
[51] Int. Cl.³ .......................... A61B 6/00; B60M 1/00; B65D 63/00
[52] U.S. Cl. ................................ 250/445 T; 24/16 R; 191/12.2 R
[58] Field of Search ................. 250/445 T; 191/12 R, 191/12.2 R; 24/16 R

[56] References Cited
U.S. PATENT DOCUMENTS

| Re. 18,460 | 5/1932 | Pieper . | |
|---|---|---|---|
| 915,288 | 3/1909 | Hagstrom . | |
| 1,225,658 | 5/1917 | Lawrence . | |
| 2,518,072 | 8/1950 | Rushworth . | |
| 3,080,017 | 3/1963 | Kent . | |
| 3,146,967 | 9/1964 | Bowman . | |
| 3,175,262 | 3/1965 | Wilson | 24/16 R |
| 3,412,951 | 11/1968 | Ober | 191/12.2 R |
| 3,601,331 | 8/1971 | Frey et al. . | |
| 3,752,180 | 7/1972 | Elder . | |
| 3,806,056 | 4/1974 | La Tour . | |
| 4,001,593 | 1/1977 | Wing | 250/445 T |
| 4,063,104 | 12/1977 | Gadd . | |
| 4,099,061 | 7/1978 | Zink et al. | 250/445 T |
| 4,146,795 | 3/1979 | Braden et al. | 250/445 T |

OTHER PUBLICATIONS

Abstract of German 26,24422 to Distler et al., Polyresearch Service, Rijswijh, Holland.

Primary Examiner—Alfred E. Smith
Assistant Examiner—T. N. Grigsby
Attorney, Agent, or Firm—Watts, Hoffmann, Fisher & Heinke Co.

[57] ABSTRACT

A cable supply and take-up for a computed tomography scanner. An annular take-up reel coacts with a cable trough configured in the shape of a segment of an annulus. The trough and guide together provide a cable slack confining space which is rectangular in cross section along any radial plane.

The trough is open at its ends. Cable is fed from a stationary external supply through one of the trough open ends and along a cable support wall to a return bend that feeds the cable to engagement with a take-up wall of the guide.

A cable bend control spongy disc provides a spring force which urges the cable into engagement with both the guide take-up wall and the trough support wall while maintaining a bend with a substantially smooth and uniform radius of curvature.

20 Claims, 5 Drawing Figures

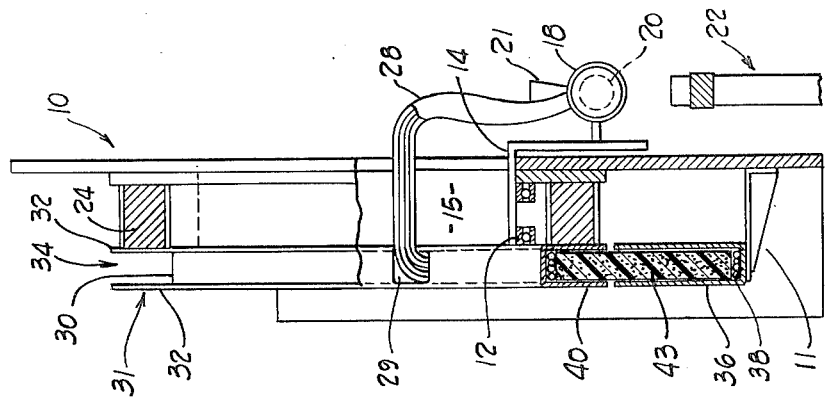
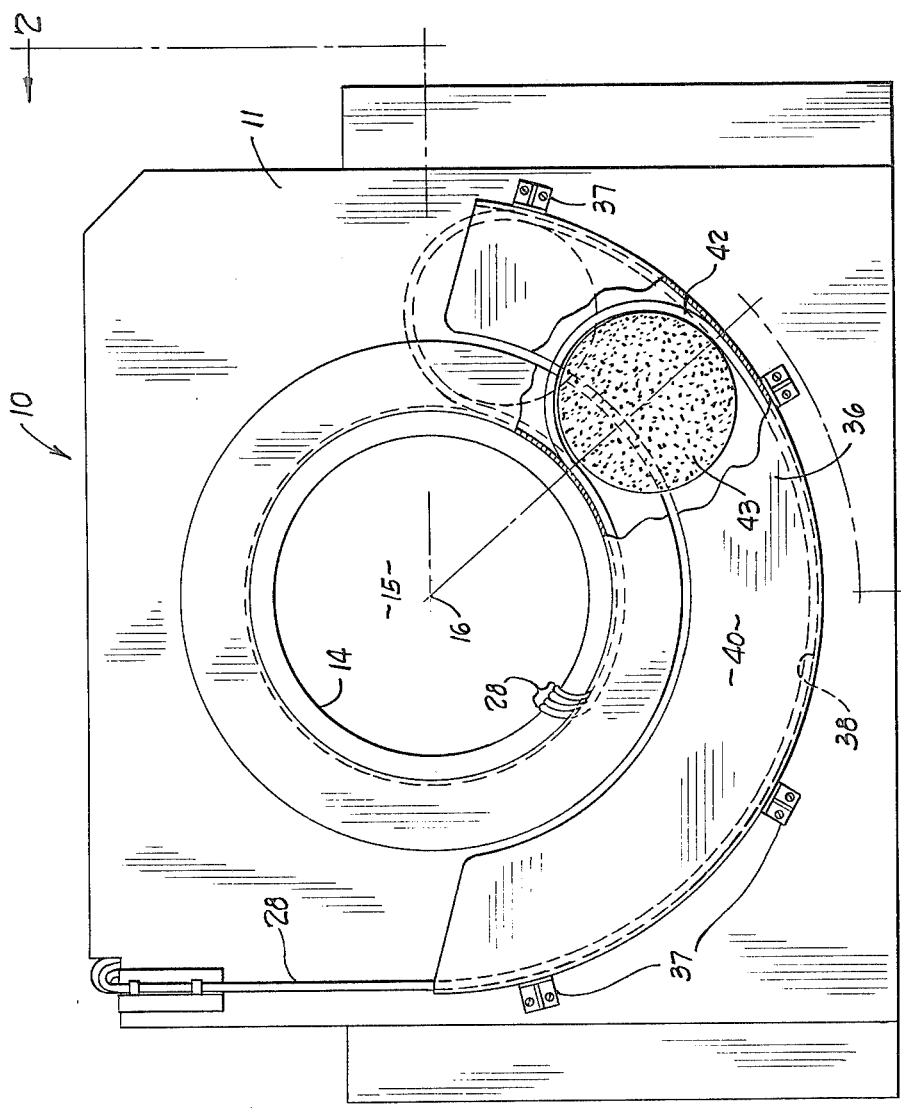

COMPUTED TOMOGRAPHY METHOD AND APPARATUS

BACKGROUND OF THE INVENTION

This invention relates to computed tomography and more particularly to a cable-handling system for use in a computed tomography machine.

Medical diagnoses are frequently made with the help of cross-sectional patient images developed through a procedure formerly known as computerized axial tomography (CAT) and now generally referred to as simply computed tomography (CT). With all current CT machines, an X-ray tube is moved in an orbital path about a patient.

With so-called translate-rotate (TR) machines, an X-ray tube and a paired detector array are moved linearly as the X-ray tube is energized and data is collected. After the lineal or translational movement along a given path has been completed, the source/detector pair are orbited incrementally typically for about 20° of rotation. After the incremental orbiting has been completed, the source and detector are scanned linearly once again and further data is collected. This alternate lineal translation and orbital motion is repeated until the desired data has been collected for production of a so-called reconstructed image.

Other machines are in use in which the X-ray tube and a connected array of detectors are orbited about an axis which intercepts the patient. Data is collected during the orbital movement.

More recently, stationary detector (SD) machines have been developed. With SD machines a fixed annular array of detectors is provided. An X-ray tube is orbited about an axis which is also the axis of the detector array. The tube is orbited at a high rate of speed so that the data collection to produce an image is completed in as little as one second.

The provision of electrical power to the X-ray tube and associated elements of a tube head assembly is essential to the operation of any of these machines. Usually the X-ray tube is of the type that employs a rotating anode and a thermionic filament. It is necessary to provide filament current to heat the filament, power to the motor which rotates the anode and the high-tension current used to direct an electron beam from the cathode to the anode. Often the tube will also be equipped with a focusing cup and/or a grid which also requires power. In addition, other components of the tube head assembly may require power. Examples are motors to drive collimator elements, a filter drive motor and a light to indicate collimator position.

In most if not all current CT machines, power is supplied to the X-ray tube head assembly through flexible conduits or cables. Since the X-ray tube is orbited about the patient, the problem of playing out and retrieving these electrical cables is considerable. The problem is magnified in that the cable must be kept free of a patient positioning aperture through the center of the machine. The problem is further complicated by the high speed, repetitive movement of the cables through an extremely high number of cycles. As a consequence, cable breakage due to so-called cable fatigue, i.e. cold working of the conductive metal, has troubled CT manufacturers and users.

There have been many proposals for dealing with so-called cable take-up in CT machines. While there have been many such proposals, non has been fully satisfactory and none has uniformly distributed the cable flexing over the entire slack portion of the cable with a controlled bend having a relatively large radius of curvature so as to minimize the cable fatigue.

SUMMARY OF THE PRESENT INVENTION

The cable take-up mechanism of the present invention distributes cable flexing substantially uniformly throughout an entire slack portion of the cable provided for the take-up function. The flexing is in a controlled bend of substantially uniform radius and lateral motion or twisting of the cables is controlled to a point where it is essentially nonexistent.

With the mechanism of this invention, an annular take-up reel is provided. The reel has a cylindrical cable take-up wall and a pair of side walls which extend radially from the ends of the take-up wall. A cable trough configured in the shape of a segment of an annulus is provided. The trough is positioned below and in alignment with the cable reel or guide.

The trough has a base cable-support wall which is configured as a segment of a cylinder and which is concentric with the cable take-up wall of the guide. The trough has side walls which are aligned with and closely spaced from the side walls of the cable guide. The trough and guide together provide a cable slack confining space which is rectangular in cross section along any radial plane.

The trough is open at its ends. The cable is fed from a stationary external supply through one of the trough open ends and along the cable support wall to a return bend that feeds the cable to engagement with the take-up wall of the guide. The cable then passes through a cable delivery opening in the guide and thence through a hollow, rotatable machine spindle. The X-ray tube is mounted on the spindle on a side opposite the guide. Thus the cable is fed through the spindle to the tube at a location which does not interfere with patient positioning through the aligned spindle and guide holes.

A cable bend control disc is provided. The disc is in the shape of a small right cylinder and is formed of sponge polyethylene in its preferred form. This disc provides a spring force which urges the cable into engagement with both the guide take-up wall and the trough support wall while maintaining a bend with a substantially smooth and uniform radius of curvature.

In use, the cable guide rotates as the spindle rotates. Thus, as the spindle rotates to produce orbital X-ray tube motion, the cable guide rotates. The cable is wound on the guide take-up wall in one direction of rotation and off it in the other. As the cable is wound on and off the take-up wall, the disc rotates about an axis which traverses a path which is a segment of an orbit about the machine's rotational axis. Thus, the disc and the bend move back and forth in the space defined by the guide and trough providing controlled and repetitive cable flexing. While the flexing is repetitive, the flexing occurs over a relatively large radius bend and the flexing is distributed uniformly over the slack portion which provides the cable for the bend.

Accordingly, an object of this invention is to provide a novel and improved cable take-up mechanism and a process of cable take-up.

BRIEF DESCRIPTION OF THE DRAWINGS

FIG. 1 is a rear elevational view of a CT machine embodying this invention with the housing removed and with parts broken away and removed for clarity of illustration.

FIG. 2 is a sectional view of the CT scanner of FIG. 1 as seen from the plane indicated by the line 2—2 of FIG. 1;

DESCRIPTION OF THE PREFERRED EMBODIMENT

Figure 3:
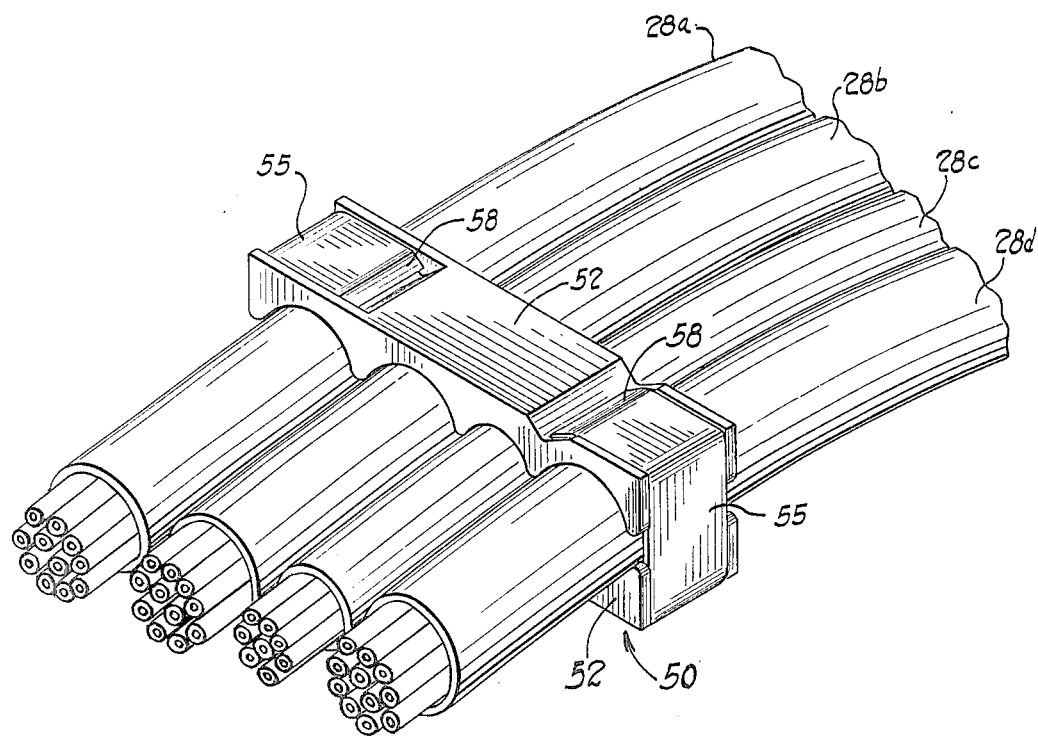
FIG. 3 is an enlarged perspective view of cable sections and a clamp for those sections.

Referring to the drawings and to FIGS. 1 and 2 in particular, the X-ray tube support and manipulating assembly of a computed tomography scanner is shown generally at 10. The assembly 10 includes a housing and frame structure 11. A pair of spindle bearings 12 are carried by the housing and frame structure 11, FIG. 2. A tubular spindle 14 is journaled in the bearings 12. The spindle 14 delineates a patient receiving opening 15. When the sanner is in use a patient is supported on a stretcher with, at least for certain studies, portions of the patient's body disposed within the opening 15.

An X-ray tube assembly 18 (FIG. 2) is fixed to the tubular spindle for orbital rotation about an axis 16 of the spindle 14 and the opening 15. The X-ray tube assembly includes an X-ray tube indicated by the dotted lines 20, a collimator shown diagrammatically at 21, and other known and conventional components of an X-ray tube assembly of the type used in CT studies.

The tube support and manipulating assembly 10 shown in FIGS. 1 and 2 is of a machine of the stationary detector type. For clarity of illustration, and because the detector array is now known in the art, the annular detector array which is around the orbital path of the X-ray tube assembly 18 is not shown except in a fragmentary schematic way at 22 in FIG. 2.

In use the X-ray tube is orbited about the axis 16 over a range of approximately 540°. This 540° range allows orbital motion over a path of sufficient length to accelerate the tube to its full speed for a study, a 360° scan and deceleration through an additional orbital path which is long enough to permit the tube to be smoothly brought to a stop. The orbital motion is first in one direction and then the other. Expressed another way, the tube may be moved through a range of 540° in a clockwise direction and then 540° counterclockwise on the next study.

A drive for this orbital motion is shown schematically and it includes an annular motor 24 which is connected to the spindle 14. The drive shown is for schematic illustration only. Any of the known and commercially-accepted drive systems can be employed.

Four flexible conduits or cables 28 are connected to the X-ray tube assembly 18. These cables include conductors for supplying power for the X-ray tube, for collimator and filter adjustment, and such other power requirements as the tube assembly may have. The cables 28 extend from the X-ray tube through the opening 15 where they are adjacent the spindle 14 and into a cable delivery opening 29, FIG. 2.

The cable delivery opening is defined by an otherwise endless and cylindrical cable take-up wall 30 of a cable guide 31. The cable guide includes a pair of radially projecting annular side walls 32 which extend from the axially spaced ends of the take-up 30. The cable guide is connected to and rotates with the spindle 14. Thus, in use, cable 28 is wound onto and off of the cable guide take-up wall as cable is fed into and out of the cable guide through a cable delivery opening 34 defined by the side walls 32.

A cable receiving trough 36 is provided. The cable receiving trough 36 is a segment of an annulus that is, over its segment, concentric with the cable guide 31. The cable supply trough 36 is fixed to the housing and frame structure 11 by supporting brackets 37. The cable 28 is fed from external supplies, one of which is an X-ray generator not shown, through the stationary housing and frame 11, into the trough 36, FIG. 1. The cable is supported by a cable support surface 38 which is defined by the trough 36. The cable support surface is a segment of a cylinder that is concentric with the cable take-up wall 30 and is coaxial with the axis 16.

The trough has a pair of side walls 40 which are radially aligned with the cable take-up side walls 32. The side walls 32, 40 are closely spaced so that the trough and cable guide define a cable supply chamber of rectangular cross section as best seen in FIG. 2. Thus the side walls 40 define a cable supply opening which is adjacent to and in communication with the cable take-up supply opening 34.

As an examination of the drawings will show, a slack portion of the cable 28 is confined within the space defined by the trough and the cable guide and that slack portion includes a controlled arcuate bend 42. A disc 43 is positioned in the bend and provides one of the outstanding advantages of the invention. The disc 43 is of a foam, spongy-like plastic material such as foamed polyethylene. The disc images the cable bend over its entire arc of about 180° and rotates as the bend moves one way or the other during cable supply and take-up. This disc contact maintains the smooth arcuate bend 42 and insures contact of the cables with the cable support surface 38 and the cable take-up wall 30.

As the spindle is rotated counterclockwise from the position shown in FIG. 1, the disc and cable will move to a fully extended position shown in phantom in FIG. 1. If the spindle is rotated clockwise with respect to FIG. 1, the cable is wound onto the take-up wall and the disc moves until it projects from the trough at the left-hand side of the drawing.

The length of the trough and the diameters of the cable take-up wall 30 and the cable support surface 38 are all selected such that the full desired 540° rotation can be obtained while the disc and bend are controlled and maintained in the cable supply space. This distributes fatigue from cable bending over the entire slack portion of the cable thus providing long and continued cable life. It also avoids any jams or other problems which might obtain were it not for the novel and improved cable supply mechanism. The supply of the cable is in a controlled and repeatable fashion so that slack take-up and dispensing is the same cycle after cycle. Thus, the trough serves as a conduit positioning means for a flexible conduit extending between two relatively rotatable elements.

Figure 5:
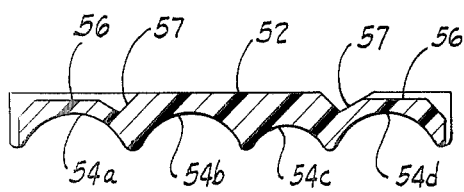
Figure 4:
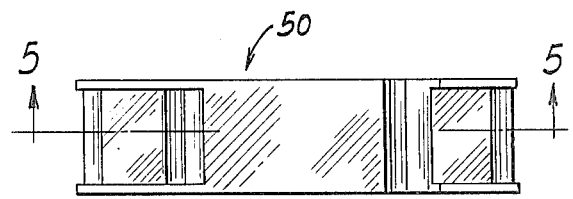
FIG. 4 is a top plan view of the cable clamp of FIG. 3 on a reduced scale with respect to FIG. 3; and, FIG. 5 is a sectional view of one of the components of the clamp assembly of FIG. 4.

The cables are maintained in alignment paralleling the axis 16 by a novel and improved clamp arrangement shown in FIGS. 3–5. In FIG. 3, a clamp assembly is shown generally at 50. A number of these clamp assemblies are mounted in spaced relationship along the slack portion of the cables. For clarity of illustration and because of the scale, they are not shown in FIGS. 1 and 2. Four cables 28A–28D are positioned such that their axes may be intersected by an imaginary straight line perpendicular to the axes. In use, this imaginary line parallels the axis 16. The cables are mounted between two molded clamp members 52 which are identical.

The clamp members 52 have cable-engaging surfaces 54A-54D which are segments of cylinders and which respectively contact the cables 28A-28D. Thus, each surface contacts a cable doing at least parallel being which locate cylinder. A pair of general U-shaped spring clips 55 are provided. The spring clips 55 are positioned in recesses 56 in the clamp elements 52.

Each of the recesses 56 includes an inclined camming and retaining surface 57. These surfaces 57 receive inwardly bent locking portions 58 of the spring clips 55. Coaction of the locking portions 58 and the camming and retaining surfaces 57 maintain the spring clips in the recesses 56 to retain the cable clamp assembly together. If one wishes to disassemble the cable clamp assembly 50, the surfaces 57 function to cam the locking portions 58 outwardly to permit removal of the spring clips and therefore disassembly of the cable clamp.

The clamps and the disc coact to maintain the cables flat against the take-up wall 30 and the cable support surface 38. The side walls 32, 40 are spaced to permit smooth cable supply and take-up action but without lateral motion. Thus, all of the elements coact synergistically to provide smooth trouble free cable supply and take-up without twisting or other problems.

Although the invention has been described in its preferred form with a certain degree of particularity, it is understood that the present disclosure of the preferred form has been made only by way of example and that numerous changes in the details of construction and the combination and arrangement of parts may be resorted to without departing from the spirit and the scope of the invention as hereinafter claimed.

What is claimed is:

1. A method of taking up a plurality of cables in a computed tomographic scanner comprising:
   (a) repetitively winding the cables from a slack portion onto and off of a rotatable cylindrical drum;
   (b) confining the slack in a cable supply space having a cable support surface concentric with the drum to form an arcuate bend in the cable; and,
   (c) maintaining the bend with a spongy disc positioned in the bend and engaging the cable.

2. A computed tomography apparatus comprising:
   (a) a housing and frame structure;
   (b) a spindle defining a patient opening and journaled on the frame structure for rotation about an axis;
   (c) an X-ray tube connected to the spindle for movement in a circular path when the spindle is rotated;
   (d) an annular cable guide connected to the spindle in axially-aligned relationship, the cable guide defining a cable delivery opening and a spaced perimetral endless cable feed opening;
   (e) a flexible cable connected to the X-ray tube guide and projecting through the delivery opening;
   (f) a cable supply trough having a cable feed opening in communication with the cable feed opening and a cable support surface spaced from the feed openings;
   (g) the cable also including a slack portion including a bend disposed at least in part within the confines of a space defined by the cable guide and the cable trough;
   (h) the cable extending outwardly of the trough for connection to an external electrical supply;
   (i) the cable guide being rotatably connected to the spindle for concurrent rotation with the cable winding onto and off of the cable guide as it is rotated in one direction and then the other; and,
   (j) a cable supporting disc disposed within the bend free of interconnection with other components of the apparatus.

3. A computed tomography apparatus comprising:
   (a) a housing and frame structure;
   (b) a tubular spindle journaled on the frame structure for rotation about an axis;
   (c) an X-ray tube connected to the spindle for movement along an orbital path when the spindle is rotated;
   (d) an annular cable guide in axially-aligned relationship with the spindle, the spindle being between the X-ray tube and the guide, the cable guide defining a cable delivery opening and a perimetral endless cable feed opening, the cable guide openings being spaced from one another;
   (e) a flexible cable connected to the X-ray tube and projecting through the spindle and the delivery opening;
   (f) a cable supply trough having a cable feed opening in communication with the cable guide feed opening and a curved cable support surface spaced from the feed openings, the cable trough also having side walls for guiding movement of the cable;
   (g) the cable also including a slack portion including a bend disposed at least in part within the confines of a space defined by the cable guide and the cable trough;
   (h) the cable extending outwardly of the trough for connection to an external electrical supply;
   (i) the cable guide being rotatably connected to the spindle for concurrent rotation with the cable winding onto and off of the cable guide as it is rotated in one direction and then the other; and,
   (j) a cable supporting disc disposed within the bend.

4. The apparatus of claim 3 wherein the disc is comprised of sponge material.

5. A computed tomography apparatus comprising:
   (a) a housing and frame structure;
   (b) a tubular spindle journaled on the frame structure for rotation about an axis;
   (c) an X-ray tube connected to the spindle for movement along an orbital path when the spindle is rotated;
   (d) an annular, hollow, cable guide connected to the spindle in axially-aligned relationship, the guide also having a radially inward, cylindrical cable take-up wall and connected, radially extending side walls, one of the walls of the guide defining a cable delivery opening and the guide's side walls defining a spaced perimetral endless cable feed opening;
   (e) the spindle and guide together defining a patient receiving opening;
   (f) the spindle being between the X-ray tube and the guide;
   (g) a flexible cable connected to the X-ray tube and projecting through the spindle opening and through the delivery opening into the interior of the guide;
   (h) a cable supply trough having a cylindrical segment shaped cable support surface concentrically spaced from the cable take-up wall and radially disposed side walls aligned with and closely spaced from the guide side walls, the trough side walls defining a cable feed opening in communication with the cable guide feed opening;

(i) the cable also including a slack portion including a bend disposed at least in part between the cable trough side walls;

(j) the trough having a cable supply opening spaced from the bend, the cable extending outwardly of the trough through the supply opening for connection to an external electrical supply;

(k) the cable guide being rotatably connected to the spindle for concurrent rotation with the cable winding onto and off of the cable take-up wall as the guide is rotated in one direction and then the other; and, (l) a cable supporting disc rotatable within and supporting the bend.

6. The apparatus of claim 5 wherein the trough is open ended and wherein one of the end openings is the supply opening.

7. A computed tomography apparatus comprising:
(a) a housing and frame structure;
(b) a spindle journaled on the frame structure for rotation about an axis;
(c) an X-ray tube connected to the spindle for movement along an orbital path when the spindle is rotated;
(d) an annular, hollow, cable guide rotatably connected to the spindle, the guide also having a radially inward, cable take-up wall and connected outwardly extending side walls, one of the walls of the guide defining a cable delivery opening and the guide's side walls defining a cable feed opening spaced from the take-up wall;
(e) a cable supply trough having a cylindrically shaped cable support wall spaced from the cable take-up wall and inwardly extending side walls generally aligned with and spaced from the guide side walls, the trough side walls defining a cable feed opening in communication with the cable guide feed opening;
(f) a flexible cable connected to the X-ray tube and projecting through the delivery opening into the interior of the guide, the cable being in engagement with the support and take-up walls;
(g) the cable also including a slack portion including a bend extending from the guide surface to the take-up wall;
(h) the cable guide being rotatably connected to the spindle for concurrent rotation with the cable winding onto and off of the cable take-up wall as the guide is rotated in one direction and then the other; and,
(i) a cable supporting circular element rotatable within and supporting the bend, the element being in cable driven engagement with the cable and maintaining the cable engagement with the take-up and support walls.

8. The apparatus of claim 7 wherein the take-up and support wall are of circular cross section and concentric and wherein the trough is below the guide such that the cable is gravity biased against the support wall.

9. The apparatus of claim 7 wherein the cable engagement with the circular element is substantially 180° in extent.

10. The apparatus of claim 7 wherein the circular element biases the cable toward the take-up wall.

11. The apparatus of claim 7 wherein there are a plurality of cables and spaced clamps engage the cables and maintain their axis perpendicular to an imaginary line paralleling the axis of rotation.

12. In an apparatus having stationary and rotatable assemblies and an electrical cable extending between the assemblies, a cable take-up mechanism comprising:
(a) an annular, hollow cable guide forming a part of the rotatable assembly, the guide having a radially inward cable take-up wall of circular cross section and connected outwardly extending side walls, one of the walls of the guide defining a cable delivery opening and the guide's side walls serving axially to confine cable wound on the take-up wall and to define a spaced perimetral endless cable feed opening;
(b) a flexible cable connected to an element of the rotatable assembly and projecting through the delivery opening into the interior of the guide;
(c) a cable supply trough having a cable support wall of circular cross section concentrically spaced from the cable take-up wall, the trough also having side walls extending from the support wall toward and aligned with the guide side walls, the trough side walls serving axially to confine cable engaging the support wall and to define a cable feed opening in communication with the cable guide feed opening;
(d) the cable also including a slack portion including a bend disposed at least in part between the side walls;
(e) the trough having a cable supply opening spaced from the bend, the cable extending outwardly of the trough through the supply opening for connection;
(f) the cable guide being rotatable winding the cable onto and off of the cable take-up wall as the guide is rotated in one direction and then the other; and,
(g) a cable supporting disc rotatable within and in supporting engagement with the bend, said disc being axially confined with the cable by the trough side walls but otherwise free of engagement with the apparatus.

13. The device of claim 12 wherein the side walls are closely spaced to define a cable supply chamber.

14. A computed tomography apparatus comprising:
(a) a housing and frame structure;
(b) a tubular spindle journaled on the frame structure for rotation about an axis;
(c) an X-ray tube connected to the spindle for movement along an orbital path when the spindle is rotated;
(d) an annular, hollow, cable guide connected to the spindle in axially-aligned relationship, the guide also having a cable take-up wall and connected, outwardly extending side walls, one of the walls of the guide defining a cable delivery opening and the guide's side walls defining a cable feed opening;
(e) a set of cables connected to the X-ray tube and projecting through the spindle opening and through the delivery opening into the interior of the guide;
(f) a cable supply trough having a cable support surface spaced from the cable take-up wall and side walls generally aligned with and closely spaced from the guide side walls, the trough side walls defining a cable feed opening in communication with the cable guide feed opening;

(g) the cables also including a slack portion including a bend disposed at least in part between the guide and trough side walls;
(h) the trough having a cable supply opening spaced from the bend, the cables extending outwardly of the trough through the supply opening for connection to an external electrical supply;
(i) the cable guide being rotatably connected to the spindle for concurrent rotation with the cables winding onto and off of the cable take-up wall as the guide is rotated in one direction and then the other;
(j) a cable supporting disc rotatable within and supporting the bend; and,
(k) a plurality of clamp elements maintaining the cables aligned along lines paralleling the axis of rotation each cable clamp comprising:
  (i) a pair of clamp elements;
  (ii) each clamp element having a plurality of recess surfaces each engaging a different cable;
  (iii) each recess surface being mated to a like surface in the other element to maintain a cable therebetween; and,
  (iv) means holding such elements together.

15. The apparatus of claim 14 wherein:
(a) each clamp element has spaced camming and retaining surfaces; and
(b) the means holding the elements of each clamp together comprises a pair of spring clamps having spaced end portions tapering toward one another and each engaging a different one of the camming and retaining surfaces.

16. A computed tomography apparatus comprising:
(a) a housing and frame structure;
(b) a tubular spindle journaled on the frame structure for rotation about an axis;
(c) an X-ray tube connected to the spindle for movement along an orbital path when the spindle is rotated;
(d) an annular cable guide in axially-aligned relationship with the spindle, the cable guide defining a cable delivery opening and a perimetral cable feed opening, the cable guide openings being spaced from one another;
(e) a flexible cable connected to the X-ray tube and projecting through the delivery opening;
(f) a cable supply trough having a cable feed opening in communication with the cable guide feed opening and a cable support surface spaced from the feed openings, the cable trough also having side walls for guiding movement of the cable;
(g) the cable also including a slack portion including a bend disposed substantially completely within the confines of a space defined by the cable guide and the cable trough;
(h) the cable extending outwardly of the trough for connection to an external electrical supply;
(i) the cable guide being rotatably connected to the spindle for concurrent rotation with the cable winding onto and off of the cable guide as it is rotated in one direction and then the other; and,
(j) a cable supporting disc disposed within the bend and axially confined by the side walls.

17. In an apparatus having stationary and rotatable assemblies and an electrical cable extending between the assemblies, a cable take-up mechanism comprising:
(a) an annular, hollow cable guide forming a part of the rotatable assembly, the guide having a radially inward cable take-up wall of circular cross section and connected outwardly extending side walls, one of the walls of the guide defining a cable delivery opening and the guide's side walls serving axially to confine cable would on the take-up wall and to define a spaced perimetral endless cable feed opening;
(b) a flexible cable connected to an element of the rotatable assembly and projecting through the delivery opening into the interior of the guide;
(c) a cable supply trough having a cable support wall of circular cross section concentrically spaced from the cable take-up wall, the trough also having side walls extending from the support wall toward and aligned with the guide side walls, the trough side walls serving axially to confine cable engaging the support wall and to define a cable feed opening in communication with the cable guide feed opening;
(d) the cable also including a slack portion including a bend disposed at least in part between the side walls;
(e) the trough having a cable supply opening spaced from the bend, the cable extending outwardly of the trough through the supply opening for connection;
(f) the cable guide being rotatable winding the cable onto and off of the cable take-up wall as the guide is rotated in one direction and then the other; and,
(g) a cable supporting disc of sponge material within and in supporting engagement with the bend.

18. A computed tomography apparatus comprising:
(a) a housing and frame structure;
(b) a tubular spindle journaled on the frame structure for rotation about an axis;
(c) an X-ray tube connected to the spindle for movement along an orbital path when the spindle is rotated;
(d) an annular cable guide in axially-aligned relationship with the spindle, the cable guide defining a cable delivery opening and a perimetral cable feed opening, the cable guide openings being spaced from one another;
(e) a flexible cable connected to the X-ray tube and projecting through the delivery opening;
(f) a cable supply trough having a cable feed opening in communication with the cable guide feed opening and a cable support surface spaced from the feed openings, the cable trough also having side walls for guiding movement of the cable;
(g) the cable also including a slack portion including a bend disposed at least in part within the confines of a space defined by the cable guide and the cable trough;
(h) the cable extending outwardly of the trough for connection to an external electrical supply;
(i) the cable guide being rotatably connected to the spindle for concurrent rotation with the cable winding onto and off of the cable guide as it is rotated in one direction and then the other; and,
(j) a cable supporting disc of sponge material disposed within the bend.

19. A computed tomography apparatus comprising:
(a) a housing and frame structure;
(b) a tubular spindle journaled on the frame structure for rotation about an axis;

(c) an X-ray tube connected to the spindle for movement along an orbital path when the spindle is rotated;
(d) an annular, hollow, cable guide connected to the spindle in axially-aligned relationship, the guide also having a radially inward, cable take-up wall and connected, generally radially extending side walls, one of the walls of the guide defining a cable delivery opening and the guide's side walls defining a spaced perimetral cable feed opening;
(e) the spindle and guide together defining a patient receiving opening;
(f) a flexible cable connected to the X-ray tube and projecting through the delivery opening into the interior of the guide;
(g) an open-ended supply trough having a cable support surface spaced from the cable take-up wall and generally radially disposed side walls aligned with and closely spaced from the guide side walls, the trough side walls defining a cable feed opening in communication with the cable guide feed opening;
(h) the cable also including a slack portion including a bend disposed at least in part between the cable trough side walls;
(i) one of the trough end openings being a cable supply opening spaced from the bend, the cable extending outwardly of the trough through the supply opening for connection to an external electrical supply;
(j) the cable guide being rotatably connected to the spindle for concurrent rotation with the cable winding onto and off of the cable take-up wall as the guide is rotated in one direction and then the other; and,
(k) a cable supporting disc rotatable within and supporting the bend.

20. In a system having a pair of relatively rotatable mechanisms connected together, an improved connecting system comprising:
(a) a flexible conduit coupled to each of the mechanisms, the conduit including slack at least partially in the form of a bend;
(b) a conduit motion control structure coactably engaging the conduit and rotatable as the mechanisms rotate relatively, the structure being adapted to take up and dispense the slack portion;
(c) a conduit positioning means including a trough around a major section of the slack portion when the system is in use, the positioning means constraining the slack portion and positioning the bend in the slack portion relative to the control structure to control the take-up and dispensing movement in a substantially repeatable fashion whereby fatigue due to source movement is minimized and spread over a significant portion of the conduit;
(d) the positioning means includes a disc within and movable with the bend, the disc being in drivable engagement with the cable and free of driving engagement with other components of the system;
(e) the side walls being closely spaced to define a cable supply chamber and the side walls confining the cable and disc in directions parallelling the axis of mechanism rotation.

* * * * *

UNITED STATES PATENT AND TRADEMARK OFFICE
CERTIFICATE OF CORRECTION

PATENT NO. : 4,246,482
DATED : January 20, 1981
INVENTOR(S) : Anton Z. Zupancic

It is certified that error appears in the above—identified patent and that said Letters Patent is hereby corrected as shown below:

Column 5, line 8, delete "doing" and substitute --along--;

line 8, after "at least" insert --three--;

line 8, delete "heing" and substitute --lines".

line 9, before "cylinder" insert --a--.

*Signed and Sealed this*

*Twenty-fourth* Day of *August 1982*

[SEAL]

*Attest:*

GERALD J. MOSSINGHOFF

*Attesting Officer*   *Commissioner of Patents and Trademarks*